(12) United States Patent
Dultz et al.

(10) Patent No.: US 7,838,285 B1
(45) Date of Patent: Nov. 23, 2010

(54) IMAGING ELECTROPHORESIS SYSTEM

(75) Inventors: Shane Dultz, Westlake Village, CA (US); David Ralin, South Pasadena, CA (US); William Rassman, Los Angeles, CA (US)

(73) Assignee: Maven Biotechnologies LLC, Pasadena, CA (US)

( * ) Notice: Subject to any disclaimer, the term of this patent is extended or adjusted under 35 U.S.C. 154(b) by 701 days.

(21) Appl. No.: 11/409,863

(22) Filed: Apr. 24, 2006

(51) Int. Cl.
*G01N 33/559* (2006.01)
*G01N 33/561* (2006.01)

(52) U.S. Cl. .......... 435/287.2; 204/450; 204/456; 204/461; 204/466; 204/400; 204/403.01; 422/82.05; 422/82.11; 435/288.7; 436/164; 436/165; 436/515; 436/516; 436/524; 436/805; 436/807

(58) Field of Classification Search .......... None
See application file for complete search history.

(56) References Cited

U.S. PATENT DOCUMENTS

| | | | |
|---|---|---|---|
| 4,238,565 A | 12/1980 | Hornby et al. | |
| 4,256,834 A | 3/1981 | Zuk et al. | |
| 4,508,832 A | 4/1985 | Carter et al. | |
| 4,558,012 A | 12/1985 | Nygren | |
| 5,229,833 A | 7/1993 | Stewart | |
| 5,255,075 A | 10/1993 | Cush | |
| 5,437,840 A | 8/1995 | King et al. | |
| 5,483,346 A | 1/1996 | Butzer | |
| 5,485,277 A | 1/1996 | Foster | |
| 5,491,556 A | 2/1996 | Stewart et al. | |
| 5,633,724 A | 5/1997 | King et al. | |
| 5,856,873 A * | 1/1999 | Naya et al. ............. | 356/369 |
| 6,594,011 B1 | 7/2003 | Kempen | |
| 6,833,920 B2 | 12/2004 | Rassman | |
| 6,859,280 B2 | 2/2005 | Kempen | |
| 6,882,420 B2 | 4/2005 | Rassman | |
| 7,002,686 B2 | 2/2006 | Lieberman | |

OTHER PUBLICATIONS

Elliott, A. The Instantaneous Monitoring of Polyacrylamide Gels during Electrophoresis, Biochem. J., 15, 743-748 (1976).
Franklin, J. and Wang, Z., Refractive Index Matching: A General Method for Enhancing the Optical Clarity of a Hydrogel Matrix, Chem. Mater. 14, 4487-4489 (2002).
Johnston, R.G., et al., Real-Time Detection of DNA During Gel Electrophoresis Using a Zeeman Refractive Index Detector, J. Biochem. Biophys. Methods, 28 (3), 1994.
Rainwater, et al., Improved Method for Making Non Denaturing Composite Gradient Gels for the Electrophoretic Separation of Lipoproteins, J. of Lipid Research, 45, 773-775.

\* cited by examiner

*Primary Examiner*—Christopher L Chin
(74) *Attorney, Agent, or Firm*—Lawrence S. Cohen

(57) ABSTRACT

Apparatus and method employing gel electrophoresis and optical imaging techniques to measure the amount of biomaterial that attaches to specified locations on a detector slide and to determine the molecular weight of the molecules at those locations.

12 Claims, 2 Drawing Sheets

IMAGING ELECTROPHORESIS SYSTEM

FIELD OF THE INVENTION

The present invention relates to detection techniques in bioanalysis, particularly optical detection during or after electrophoresis, and more particularly to such technique operative to permit imaging and real time detection of molecular binding events of molecules from a specimen onto a surface.

BACKGROUND OF THE INVENTION

Electrophoresis instruments and particularly gel electrophoresis instruments are commercially available. Conventionally, these instruments operate to move molecules of a specimen, typically DNA, RNA, proteins or peptides, in a polyacrylamide or agarose gel via electrical forces. This gel acts as a "molecular sieve" separating molecules by mass and charge. An electrical field, generated by electrodes placed on either side of the gel, forces molecules to drift through the viscous gel matrix with a drift velocity largely determined by the molecular weight of a class of molecules, the strength of the field, size and shape of the molecules, relative hydrophobicity of the sample and the ionic strength and temperature of the specimen buffer solution. Over time in a typical gel, molecules distribute in band patterns which can be subsequently stained for visualization. Using this technology, it is possible to separate and identify protein molecules that differ by as little as 1% of their molecular weight when run carefully in a gradient gel for example. This well known technique has become one of the staple tools used in molecular biology for genetic manipulation and study, DNA and protein purification, SDS PAGE, DNA footprint analysis, molecular binding studies, etc.

U.S. Pat. No. 4,558,012 to Nygren, et al issued Dec. 10, 1985, discloses the use of an ellipsometry apparatus for sensing the distribution of biomaterial in an electrophoresis operation. The Nygren patent discloses a technique in which light is reflected from the top surface of a substrate over which a gel layer is formed, the substrate having an opaque bottom surface, the light exhibiting a change in reflection intensity due to the presence of the biomaterial. The present invention differs in several respects which are necessary for more sensitive detection of thousands of molecules simultaneously. The first of these is the use of total internal reflection, described below, which monitors molecular transport within close proximity of the transparent surface. The second is the ability to image large regions of the surface in real time which is important for analyzing reaction kinetics on thousands of microarray spots for example.

U.S. Pat. Nos. 6,594,011 and 6,859,280, issued to Kempen on Jul. 15, 2003 and Feb. 22, 2005 respectively, the entire contents of which are incorporated by reference herein, disclose optical equipment for imaging binding events between patterns of probes immobilized on a surface of an optically transparent substrate and analytes to which those probes are exposed. The optical system is operative to direct polarized light to the underside of a substrate in a manner to generate an evanescent field in the plane of the probes. The equipment obtains an image of the localized changes in light intensity that occur when a probe and an analyte combine.

Most surface sensitive techniques, such as ellipsometry, cantilever detection methods, surface plasmon resonance and quartz crystal microbalance, measure the total mass of molecules within a specified region on a surface. It is therefore, very difficult to distinguish regions of the surface where multiple molecular species, often of varying mass, may adsorb. This ultimately restricts lower limits of detection of particular molecules in solution due to the presence of non-specific interactions, and complicates analysis of specific competitive reactions. This has become one of the biggest problems facing researchers working with label-free technologies.

In accordance with the present invention, the optical imaging system described in U.S. Pat. Nos. 6,594,011 and 6,859,280 and gel electrophoresis are combined in an apparatus that can measure not only the amount of biomaterial distributed over a detector slide but also the molecular weight of the molecules so distributed. In contrast to typical optical systems used, for example, in the above referenced patent to Nygren, the apparatus of the invention is not based on light absorption and does not require that the underside of the substrate be opaque. As such, the invention operates with a specimen placed in the evanescent field of a reflected light beam to provide improved imaging resolution and signal strength.

REFERENCES

| U.S. Patent Documents | | |
|---|---|---|
| 4,558,012 | December, 1985 | Nygren, et. al. |
| 5,856,873 | January, 1999 | Naya, et. al. |
| 6,594,011 | July, 2003 | Kempen |
| 6,833,920 | December, 2004 | Rassman, et. al. |
| 6,859,280 | February, 2005 | Kempen |
| 6,882,420 | April, 2005 | Rassman, et. al. |
| 7,002,686 | February, 2006 | Lieberman, et. al. |

OTHER REFERENCES

Franklin, J. and Wang, Z., Refractive Index Matching: A General Method for Enhancing the Optical Clarity of a Hydrogel Matrix, Chem. Mater. 14, 4487-4489 (2002).

Elliott, A., The Instantaneous Monitoring of Polyacrylamide Gels during Electrophoresis, Biochem. J., 159, 743-748 (1976).

Pierscionek, B. K., Refractive Index of the Human Lens Surface Measured with an Optic Fiber Sensor, Ophthalmic Research, 26 (5), pp. 324 (1994).

Rainwater, et. al., Improved Method for Making Non Denaturing Composite Gradient Gels for the Electrophoretic Separation of Lipoproteins, J. of Lipid Research, 45, 773-775 (2004).

Johnston, R. G., et. al., Real-Time Detection of DNA During Gel Electrophoresis Using a Zeeman Refractive Index Detector, J. Biochem. Biophys. Methods, 28 (3), 225-237 (1994).

DETAILED DESCRIPTION OF THE INVENTION

Figure 1:
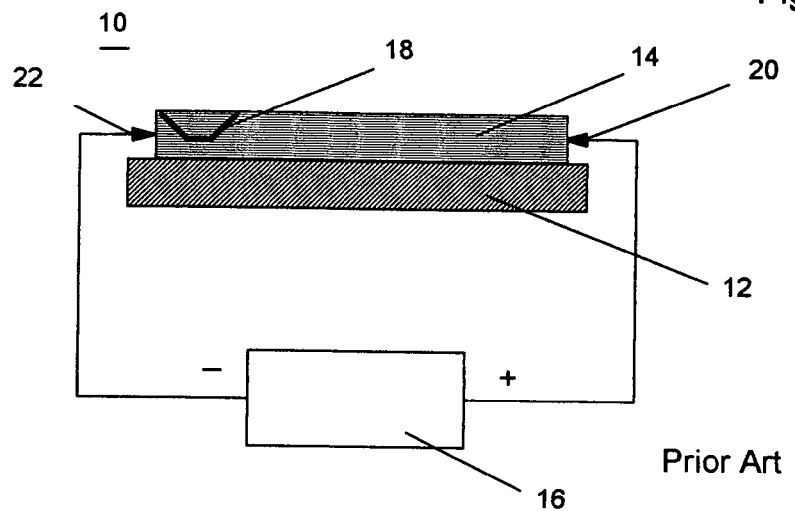
FIG. 1 is a diagram of an electrophoresis device.

With reference to FIG. 1, a basic gel electrophoresis apparatus 10 is functionally illustrated comprising a substrate 12, a gel 14 deposited on the substrate, a power supply 16 connected to an anode electrode 20 and a cathode electrode 22.

The electrodes are connected at opposite ends of the gel to provide an electrical current therethrough.

In operation, a biological sample, such as proteins or DNA molecules in a buffer solution, is introduced to a sample loading well 18 cut out in the gel. The power supply provides electrical current to move the molecules through the gel between the electrodes.

Figure 2:
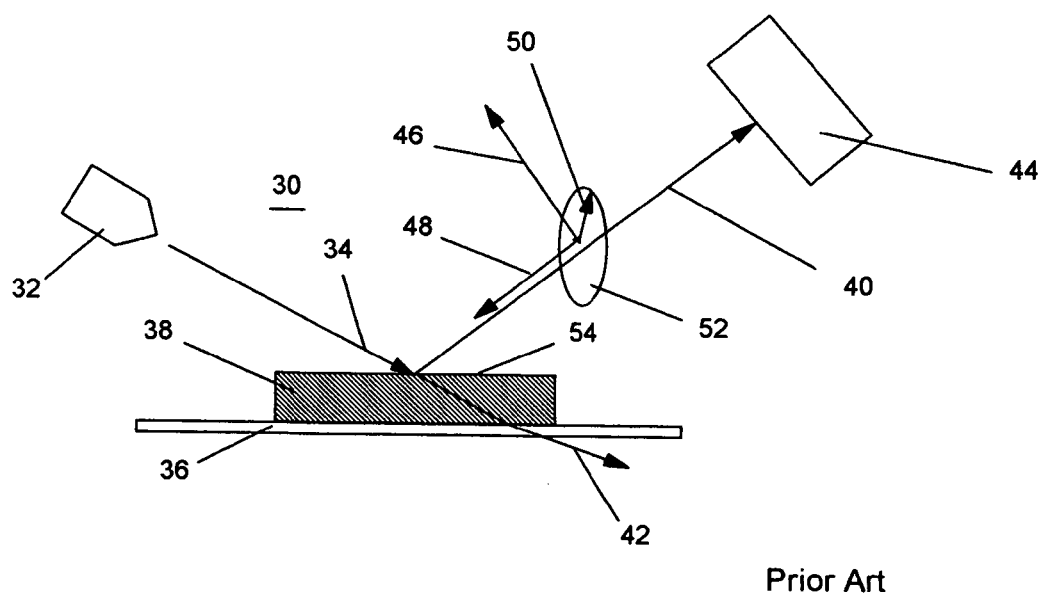
FIG. 2 is a diagram of an optical ellipsometric device.

With reference to FIG. 2, typical optical ellipsometric apparatus 30 employ a light source 32 to project an incident beam of light 34 on a sample 38 and a polarization-sensitive device 44 to analyze reflected light 40 from the surface 54 of the sample.

At the sample surface 54, part of the incident light is reflected and part of the light is transmitted. As illustrated, the incident light beam 34 can be split into component parts comprising a reflected light beam 40 and a transmitted light beam 42.

If the polarization of the incident light beam is known, analysis of the change in polarization of the transmitted or reflected light beams can be used to determine nanoscale information about the sample material, including properties such as index of refraction, extinction coefficient, thickness, roughness, void fraction, uniformity, and anisotropy. A detailed description of the principles of ellipsometry can be found in many references including (Ellipsometry and Polarized Light, Azzam and Bashara, 1987) and (Handbook of Ellipsometry, Tompkins and Irene, 2005).

Figure 3:
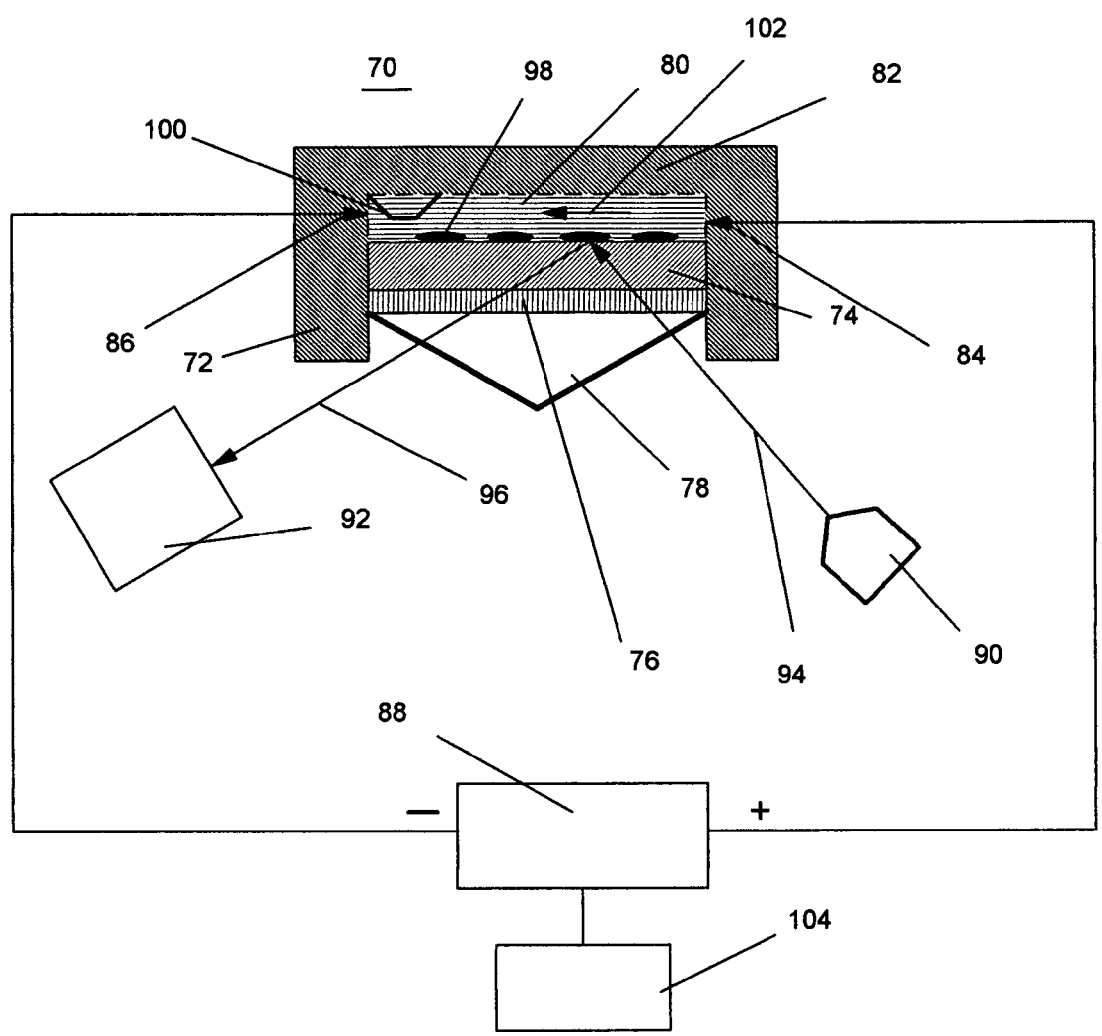
FIG. 3 is an illustration of an apparatus of the invention.

With reference to FIG. 3, an apparatus of the invention comprises a cassette 70 adapted to hold a transparent slide 74 on which a gel layer 80 is deposited. The gel layer overlies one or more patterns of probes or spots 98 for binding with analyte molecules in a sample to be analyzed. The sample to be analyzed is introduced into the gel layer through a sample loading well 100 cut out of the layer material. The cassette has side wells 72 adapted to contain a buffer solution 82 for electrophoresis measurements. As shown, a positive electrode 84 and a negative electrode 86 from a power supply 88 are connected through the cassette to provide electrical connections to the gel layer to produce the required electric field 102. An electric field controller 104 is connected to the power supply to control the direction and intensity of the applied electric field.

The preferred embodiment of the invention uses a total internal reflection (TIR) evanescent field type of imaging system, as described for example in the above referenced patents incorporated by reference herein, and can comprise a light source assembly 90 producing an elliptically polarized light beam 94 to illuminate a sample placed on the transparent slide 74. TIR imaging has the advantage that the path of the light beam is not influenced by subtle changes in the index of refraction of the surrounding liquid. Further advantages include the ability to image molecular attachment in turbid and opaque liquids and the ability to use infrared wavelengths where imaging through a buffer solution would be impossible.

An optical element such as a prism or grating 78 is used to direct light to and from the sample to a polarization-sensitive imaging system 92. An index-matching oil or polymer layer 76 is placed between the slide and the prism to index match the contact surface of the prism to the contact surface of the slide. In a preferred embodiment of the invention, the slide is configured with microarray target spots 98 consistent with the high throughput aspects of the current technology (U.S. Pat. Nos. 6,594,011, 6,833,920).

In one embodiment of the invention, an electric field is operative to move components of a sample of analytes, introduced into the gel from the sample loading well, over patterns of probes or spots placed in the evanescent field of the reflected light beam 96. An imaging system 92 captures an image of the pattern of binding events between probes and analytes enabling not only the identification of which analytes are present in the sample but also the molecular weight of the analyte in each instance. Furthermore, the electrophoresis process may be imaged directly while the molecules migrate within the gel. Currently, this can only be done if the molecules of interest are labeled beforehand with a visible dye.

Molecules with the lowest molecular weight will move faster through the gel and will separate from the rest of the sample in bands. As the sample distribution emerges, the imaging system detects the motion of the material as long as sufficient molecules exist within the narrow surface volume near the slide/gel interface. At this point, the molecular weight and amount of material can be estimated as it passes over target spots on the array. The chemical composition of specific spots on the array will tend to remove material from the passing band in a way consistent with the affinity of the local reaction.

A variety of sample analysis options are available within this particular embodiment. One option for advanced sample measurements is to alternately change the direction of the applied electric field during electrophoresis, allowing the bands of biomolecules to make numerous passes over individual microarray spots or localized targets. One high affinity reaction, for example, may require a single pass to remove 90% of the molecules within the evanescent field whereas a lower affinity reaction may require several passes to remove only a small percentage of the molecules.

In another embodiment of the invention, gel electrophoresis is performed strictly as a molecular purification of analytes upstream of target spots on the detector slide. As the separated bands leave the end of the gel matrix, they move into a fluid stream medium which delivers the analytes to the slide target spots. This fluid stream continually flows over a detector region of a slide where TIR imaging is performed on spots containing capture molecules for the analytes of interest. Measurements are made continuously to yield information about the quantity of material in each molecular weight category attaching to each array spot since the time of arrival of molecules to the surface is indicative of the molecular weight of such molecules.

FIG. 3 shows an electric field 102 that is parallel to the slide surface and in a single direction. In addition, a second field in the y-direction could be introduced to steer molecules toward desired locations on the slide surface or perform a 2D gel before bringing molecules to the evanescent field region.

Electrodes sandwiching the gel can also be placed to move molecules in a perpendicular direction, toward or away from the surface of the slide. This configuration would be particularly useful for thick layer materials and allows the detection time to be controlled by controlling the electric field to speed reactions, rather than rely strictly on molecular diffusion in aqueous solution. An appropriate field can be generated by sandwiching the gel layer between a pair of electrodes, one of which makes up the sensing surface. Such a field can be used with or without the horizontal fields to move molecules toward or away from the surface, to concentrate analyte near the surface, to speed adsorption and improve sensitivity. In addition, the field can be used to retard non-specific adsorption, remove unbound materials and thereby improve or test specificity. In combination, this embodiment constitutes three-axis electrophoretic control of molecular movement through a gel. Gel configurations can include planar and capillary electrophoresis types.

The gel can be a standard electrophoresis gel such as agarose or polyacrylimide, effective to reduce the mobility of biomolecules in the presence of an applied electric field, but may also be any low or high index material that enhances the sensitivity of imaging measurements. There are known polymers, for example, which have the ability to act as molecular sieves and there are advantages in this particular application for the use of materials which have higher refractive indices than agarose or polyacrylimide.

Various electrode geometries on the surface of the glass slide can also be used to provide molecular separation techniques more complex than the standard one-dimensional separation of molecules through the gel matrix.

An apparatus of the invention would simplify and significantly reduce the time it takes to perform the Western Blot process from days to 30-60 minutes without any labeling or incubation steps.

A typical Western Blot takes one to two days of manual labor with 100-200 different pipetting steps (Cahill, Cell Biosciences). The first step is gel electrophoresis. The proteins are separated by molecular weight on a gel using SDS-PAGE.

The next step usually involves the transferring of proteins from the gel to a nitrocellulose membrane. This step is not necessary for this invention since the protein band separations are constantly being imaged using TIR imaging ellipsometry.

Once the proteins sufficiently separate by molecular weight and/or isoelectric point, a blocking protocol is necessary, as in a Western Blot, so that antibodies, for example, are less likely to non-specifically bind to the gel or nitrocellulose transport layer.

As antibodies are moving over the surface in solution, real time attachment of the antibody to only proteins of interest is seen as the reflectivity of polarized light changes during binding. This experiment may be repeated multiple times to identify, in series or in parallel, multiple proteins and quantify the number of specific proteins within each band.

Although the various features of novelty that characterize the invention have been described in terms of certain preferred embodiments, other embodiments will become apparent to those of ordinary skill in the art, in view of the disclosure herein. Accordingly, the present invention is not limited by the recitation of the preferred embodiments, but is instead intended to be defined solely by reference to the appended claims.

What is claimed is:

1. Apparatus comprising a light source for emitting a beam of polarized light, said apparatus also including a light reflection surface arranged such that said light beam is reflected from the light reflection surface at an angle to provide an evanescent field above the light reflection surface, said light reflection surface having an array of probes placed thereon in said evanescent field, said apparatus also including a detector positioned to detect polarization changes in said reflected light beam caused by localized binding events between probes of said array and analyte molecules of a sample said apparatus including a gel layer above said probes; and
    a first means for generating an electric field in said gel layer extending laterally with respect to said reflection surface for moving by electrophoresis functioning molecules of a sample introduced to said gel layer laterally with respect to the array of probes.

2. Apparatus as in claim 1 said array of probes having a plurality of probe patterns in which each probe pattern is functional for binding detection of a different analyte.

3. Apparatus as in claim 1 also including a second means for generating a second electric field perpendicular to said first electric field.

4. Apparatus as in claim 1 wherein said array of probes is located in a first portion of said light reflection surface spaced laterally apart from a sample supply area and said electric field is operative in a second portion of said light reflection surface between said sample supply area and said first portion to separate by molecular weight in said gel layer the molecules of a sample introduced at said sample supply area.

5. A system for enhancing chemical detection and analysis comprising:
    a transparent substrate having a top surface;
    a gel layer over the top surface;
    a source of an electric field operative by electrophoresis functioning to move molecules within the gel layer along one or more selected paths laterally with respect to the top surface;
    one or more arrays of probe patterns on the top surface;
    wherein the one or more selected paths are determined based on selected proximity to the one or more arrays of probe patterns;
    whereby molecules being moved by electrophoresis are caused to traverse a path proximate the one or more arrays of probe patterns in order to enhance the occurrence of binding events; and
    an apparatus to effect total internal reflection imaging ellipsometry to create an evanescent field above the top surface such that the probe arrays are in the evanescent field said apparatus using a source of polarized light to enable detection of polarization state information caused by binding events to the probe array.

6. The system of claim 5 further comprising:
    a plurality of probe patterns on the substrate each probe pattern being functional for binding detection of a single specific molecule;
    the probe patterns being arranged in an order relative to the electrophoresis functioning path of movement of molecules such that the molecules will be arranged in the same order.

7. The system of claim 5 further comprising:
    a light source for emitting a beam of polarized light, arranged such that said light beam is reflected from the top surface in a manner to provide an evanescent field above the top surface such that the probes are in the evanescent field; and
    a polarization sensitive imaging system arranged to receive and process the reflected light whereby binding events can be imaged.

8. The system of claim 7 further comprising:
    a plurality of probe patterns on the substrate each probe pattern being functional for binding detection of a single specific molecule;
    the probe patterns being arranged in an order relative to the electrophoreses functioning path of movement of molecules such that the molecules will be arranged in the same order;
    wherein binding events will be organized according to the order of arrangement of probes.

9. The system of claim 5 further wherein said electric field defines a first electric field operative to move molecules through the gel layer in a first lateral direction relative to the array patterns and further comprising a second electric field at a right angle to the first electric field operative to move molecules in a second lateral direction relative to the array patterns which is at a right angle to the first lateral direction.

10. The system of claim 5 further wherein said electric field defines a first electric field operative to move molecules through the gel layer in a first lateral direction relative to the array patterns and further comprising an additional electric field operative to cause said molecules to traverse a path in a vertical direction relative to the array patterns.

11. A cassette including a slide having a top and a bottom surface, an array of probes on at least a portion of said top surface and a gel layer on said probes, said cassette also including means for generating an electric field in said gel layer for moving analyte molecules in said gel layer laterally with respect to said probes, wherein said slide is transparent and operative to transmit light from said bottom to said top surface in a manner to generate an evanescent field above said top surface.

12. A system for enhancing chemical detection and analysis comprising:
    a transparent substrate having a top surface:
    a gel layer on the top surface;
    a source of an electric field operative by electrophoresis functioning to move molecules within the gel layer along one or more selected paths laterally with respect to the top surface;
    one or more arrays of probe patterns on the top surface;
    wherein the one or more selected paths are determined based on selected proximity to the one or more arrays of probe patterns;
whereby molecules being moved by electrophoresis are caused to traverse a path proximate the one or more arrays of probe patterns in order to enhance the occurrence of binding events; and
an imaging apparatus comprising;
    a light source emitting a polarized beam of light said light source being directed at the transparent substrate to be totally internally reflected at the top surface and to provide an evanescent field such that the one or more arrays of probes are in the evanescent field such that the one or more array of probes in the evanescent field causes spatially distributed polarization changes in the cross-section of the light beam; and
    a detector positioned to detect the spatially distributed polarization changes caused by the probes.

* * * * *